United States Patent [19]

Hauser

[11] 4,187,851
[45] Feb. 12, 1980

[54] SHEATH ARRANGEMENT FOR MALE URINAL DEVICE AND METHOD OF FORMING THE SAME

[75] Inventor: Thomas M. Hauser, St. Paul, Minn.

[73] Assignee: Mentor Corporation, Minneapolis, Minn.

[21] Appl. No.: 716,112

[22] Filed: Aug. 20, 1976

[51] Int. Cl.[2] .............................................. A61F 5/44
[52] U.S. Cl. ..................................... 128/295; 128/157; 128/169
[58] Field of Search ............. 128/294, 295, 157, 165, 128/169, 170

[56] References Cited

U.S. PATENT DOCUMENTS

| | | | |
|---|---|---|---|
| 2,687,723 | 8/1954 | Stern | 128/169 |
| 3,631,857 | 1/1972 | Maddison | 128/295 |
| 3,863,638 | 2/1975 | Rogers et al. | 128/295 |

Primary Examiner—Robert W. Michell
Assistant Examiner—J. L. Kruter
Attorney, Agent, or Firm—Kinney, Lange, Braddock, Westman and Fairbairn

[57] ABSTRACT

A sheath arrangement for a male urinal device having a urinal sheath of flexible material, designed for application to a penis for covering a substantial portion thereof lengthwise of the same and having a lower portion for connection to a urine receptacle, and a liner pad of resilient, compressible, deformable, waterproof material in the form of a strip of such material having a width sufficiently narrow to allow the strip to be wound spirally to extend over a portion of the penis beneath the sheath much greater in length than the width of the strip. The material of the pad is sufficiently deformable to ensure liquid tight engagement of the overlapping portions of the pad with the penis. Preferably, both the inner surface and the outer surface of the pad are adhesive so that not only is the liner pad held in place on the penis but the sheath is also held against movement with respect to the liner pad. The sheath arrangement is formed by spirally winding the liner pad firmly around the penis. The sheath in rolled-up form is then placed in position on the penis adjacent the glans thereof and the sheath is unrolled so as to extend completely over the liner pad. The sheath is then gently squeezed to ensure that the overlapping portions of the liner are sufficiently deformed to conform with the surface of the penis and that the liner adheres to the penis and sheath to form a liquid tight seal with the penis.

2 Claims, 7 Drawing Figures

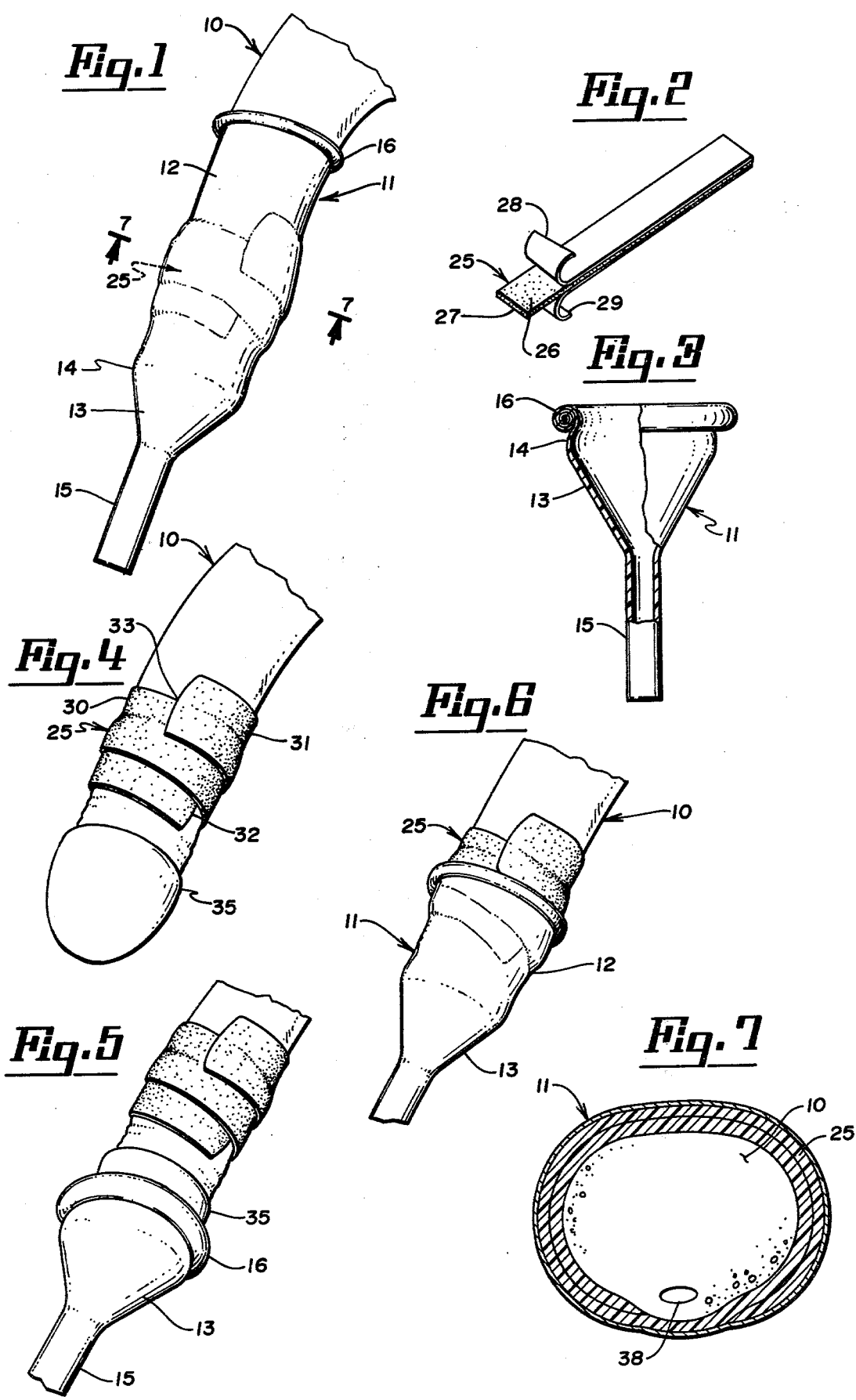

SHEATH ARRANGEMENT FOR MALE URINAL DEVICE AND METHOD OF FORMING THE SAME

BACKGROUND OF THE INVENTION

In the Rogers et al U.S. Pat. No. 3,863,638, there is disclosed an improved sheath arrangement for a male urinal device in which there is interposed between a flexible sheath and the penis on which the sheath is applied, a liner pad of resiliently compressible, deformable, waterproof material in the form of a relatively wide strip to be wound around the penis to form a cushion between the penis and the sheath. In the arrangement of the prior aforesaid patent, the liner pad is wide enough to extend from the head of the penis upwardly along the penile shaft a sufficient distance to provide an adequate cushion between the sheath and the penis. Within this prior arrangement, at least the inner surface of the liner pad is provided with an adhesive so as to cling to the penis.

While the arrangement of U.S. Pat. No. 3,863,638 has proven to be a marked improvement over prior sheath arrangements, it has the drawback that if the strip is made wide enough to cover an adequate length of the penis for a relatively long penis, it is too wide for use in connection with a relatively short penis. As a result, it has been necessary to use a strip which is narrower than desirable for a long penis to insure that it will not be too wide for a short penis.

SUMMARY OF THE PRESENT INVENTION

The present invention is concerned with a sheath arrangement of the type discussed employing a urinal sheath of flexible material and a liner pad of resiliently compressible, deformable, waterproof material in which the strip is relatively narrow and is spirally wound so as to extend along the penile shaft a sufficient distance to provide an adequate cushion between the sheath and the penis. The strip is preferably sufficiently long to permit sufficient turns of the spiral strip to cover an adequate length of the penis.

At least the inner surface of the liner strip is adhesively coated so as to adhere to the penis and to aid in the overlapping turns of the strip adhering to one another. Preferably, the outer surface of the liner pad strip is also adhesively coated to insure that the sheath is retained in position with respect to the liner pad.

The width of the liner pad strip preferably is not over one inch so that the liner pad can be spirally wound even on a relatively short penile shaft. The thickness of the liner pad strip is preferably less than one-eighth of an inch so that overlapping turns of the strip will not result in an excessively thick liner pad.

The present application is also concerned with a novel method of forming a sheath arrangement in which a liner pad strip of the type discussed above is spirally wound around the penile shaft with sufficient tension that the deformable material of the pad is deformed to conform closely with the surface of the penile shaft.

In this novel method, after the liner pad has been spirally wound around the penis, the sheath is placed adjacent the glans of the penis with the major thin wall of the sheath rolled up. The sheath is then unrolled over the spirally wound pad until the unrolled portion extends above the upper extremity of the spirally wound liner pad. Even though the exterior surface of the liner pad is adhesively coated, it is possible by this method to roll the sheath over the adhesive surface of the liner pad with the result that the sheath is held firmly in position with respect to the liner pad. After the sheath is unrolled over the liner the sheath is gently squeezed to press the various elements together to effect a liquid tight seal and to ensure that the sheath is held in place on the liner.

Various other objects and features of the invention will be apparent from a consideration of the accompanying specification, claims and drawing.

BRIEF DESCRIPTION OF THE DRAWING

FIG. 1 is a perspective view of a penis with my improved sheath arrangement secured thereto;

FIG. 2 is a perspective view of the liner pad strip with portions of the protective backing partially pealed away;

FIG. 3 is an elevational view, with portions in section, of my improved sheath arrangement;

FIG. 4 is a perspective view of a penis with the liner pad applied thereto but without the sheath;

FIG. 5 is a view of a portion of a penis with the liner pad applied thereto and with the sheath in the initial position in which it is placed prior to unrolling the same over the liner pad;

FIG. 6 is a view similar to FIG. 5 but with the sheath partially unrolled over the liner pad; and FIG. 7 is a sectional view taken through the line 7—7 of FIG. 1.

DESCRIPTION OF THE PREFERRED EMBODIMENT

Referring to FIG. 1, the sheath arrangement is shown in position. The sheath is designated in its entirety by the reference numeral 11, being shown in rolled up form in FIG. 3. Referring to FIG. 1, the sheath has a very thin body portion 12 joined at 14 to a conical portion 13 which terminates in a tubular portion 15. The tubular portion 15 is connected through any suitable means to a suitable urine receptacle (not shown). A typical arrangement of this type is shown in the Rogers et al U.S. Pat. No. 3,835,857, granted September 17, 1974. The conical portion 13 and the tubular portion 15 are preferably formed of relatively heavy material integral with the thin body portion 12. The body portion 12 is formed of very thin resilient material capable of being rolled up over the penis 10. Initially, before it is applied to the penis, the body portion 12 is completely rolled up as shown in FIG. 3.

An important feature of the present invention is the liner pad employed in connection with the sheath 11. As noted above, one of the novel features of the present liner pad is that it is relatively narrow so that it can be wound spirally over even a relatively short penile shaft. As best shown in FIG. 2, the liner pad 25 is in the form of a strip of material, preferably not over 1 inch in width and not over one-eighth of an inch in thickness. The liner pad may be formed of a suitable resilient deformable material which has been expanded to form a closed cell foam structure. It is essential that the material not only be resiliently compressible but also deformable. It is also essential that the material be waterproof. There are a variety of materials which are suitable for this purpose. A typical material of this type is a blend of nitro rubber and polyvinyl chloride, such as is disclosed in the Daly et al U.S. Pat. No. 2,570,182, granted Oct. 9, 1951. This material is sold under the trade name Ensolite by Uniroyal, Inc. Secured to the opposite surfaces of this material are adhesive layers 26 and 27 of a pressure sensitive adhesive. Any suitable pressure sensitive adhesive which is non-irritating is employed. Secured to the adhesive layers 26 and 27 are liner strips 28 and 29 used to prevent the adhesive layers 26 and 27 adhering to other objects until the liner pad is to be used.

In use, the liner strips 28 and 29 are removed and the liner pad 25 is spirally wrapped around the penis relatively firmly. As the liner pad is wound firmly about the penis 10, the liner pad 25 tends to be deformed so as to lay against and conform with the surface of the penis despite the overlapping turns of the strip 25. Thus, in FIG. 4, the outermost portion 30 of the second turn is depressed inwardly against the penis with respect to the portion of the turn overlapping the previous turn of strip 25. The same effect can be observed with the portion 31 of the uppermost turn of the strip 25.

As has been previously noted, the inner surface 27 of the strip is provided with an adhesive layer. This not only causes the strip to adhere to the penis 10 but it also causes the overlapping portions of the turns of the strip to adhere to each other. As a result of the strip being provided with this adhesive coating and as a result of the strip being deformable, the liner strip forms a waterproof pad in which there are no internal channels through which urine might flow. For example, if the strip 25 were not readily deformable and was not provided with an adhesive surface, it would be possible for urine to enter a passage adjacent the lower end 32 of the strip and then to travel along a helical passage following the upper edge of the strip. The urine travelling this passage could then emerge at point 33. Thus, if the wearer was in a reclining position or in bed, urine could travel back along the path just traced and under the upper portion of the thin body part 12 of the sheath so as to emerge at the top of the sheath. With my improved construction, however, this is prevented.

As previously pointed out, the sheath initially takes the form shown in FIG. 3 in which the upper body portion is rolled up to the junction portion 14. The drawing of FIG. 3 does not, of course, correctly show the number of turns in the rolled bead 16. Due to the thin nature of the sheath, there will be a very large number of turns in this rolled up portion 16. In order to apply the sheath, it is placed in the position of FIG. 5 in which the inner wall of the conical portion 13 engages the glans 35 of the penis 10. The sheath is then unrolled substantially as shown in FIG. 6 so that the body portion 12 extends progressively further along the penis. Since the action is a rolling action, it is possible to move the sheath over the liner pad 25 despite the fact that the liner pad has an adhesive uter coating. This unrolling action is continued until the sheath is in the position shown in FIG. 1. It will be noted that at this point the unrolled portion 16 is relatively small and is well above the topmost edge of the liner pad 25. After the sheath has been unrolled, it is gently squeezed to ensure that the overlapping portions of the liner are sufficiently deformed to conform with the surface of the penis that the liner adheres to the penis and that the sheath adheres to the liner.

The sheath arrangement of FIG. 1 formed in the manner described is a liquid tight, very comfortable, sheath arrangement. Because of the spiral winding of the strip to form the liner pad 25, it extends over a substantial portion of the penis and exerts a minimum constricting effect. Furthermore, it is completely liquid tight because of the overlapping portions of the strip being deformed to conform to the surface of the penis. The liquid tight seal between the pad and the penis is also enhanced by the adhesive coating which causes the overlapping turns to adhere to each other and the liner pad to closely adhere to the surface of the penis. Because of the adhesive outer coating, the sheath 11 is held firmly in position against displacement with respect to the liner pad 25. Since the sheath is preferably made of thin resilient material such as latex, it is resilient and closely conforms with the outer surface of the pad and with the surface of the penis above the pad. The unrolled bead 16 of the liner 11 further tends to hold the sheath 11 in position and to guard further against any possible leakage.

The liner pad of the present invention has relatively little constricting effect upon the penis and upon the urethral passage. It will be noted from FIG. 7 that the urethral passage 38 passes close to the under wall of the penis. Obviously, if the strip 25 were a narrow strip which was wound tightly around a narrow portion of the penis, there would be a tendency to constrict the passage of urine through the passage 38. In view, however, of the fact that the spirally wound strip extends over a substantial portion of the penis, the constricting effect of the liner pad 25 is minimized.

I prefer to use a diposable sheath 11 and liner pad 25. When it is desired to remove the sheath 11, all that it is necessary to do is to roll the sheath and liner together downwardly until they are rolled off the end of the penis. Despite the adhesive coatings on the liner, it is possible by the rolling action to remove the sheath and liner at the same time without discomfort to the patient.

CONCLUSION

It will be seen that by the use of a spiral strip, comprising at least one adhesive coating and being made of resiliently compressible, deformable material, it is possible to obtain a liner pad which is spirally wound and can be adjusted readily to conform with the portion of the penis on which the sheath is being applied. This makes it possible to have a single width of liner pad and still properly cover the penis. Where the penile shaft is relatively long, the adjacent turns will not be overlapped to as great an extent so that the tape extends over a greater length of the penile shaft. Where, however, the penile shaft is relatively short, the turns will be overlapped to a greater extent and thus will cover a smaller length of the penis. This, moreover, is accomplished without any increase in discomfort to the wearer and without any constriction of the urethral passage.

While I have shown a specific embodiment of my invention and have described a specific method of applying the sheath, it is to be understood that various modifications are possible and that the scope of the invention is limited solely by the appended claims.

I claim:
1. The method of applying a urinal sheath to a penis which comprises:
   providing a liner pad of resiliently compressible, deformable waterproof material in the form of a thin strip of such material having a width substantially less than the portion of the sheath intended to extend over the penis and of a length at least one and a half times the circumference of a normal flaccid penis, the inner and outer surfaces of the liner pad both being adhesive.

winding said strip spirally around said penis over a length of the penis much greater than the width of the strip and applying sufficient pressure during winding that the overlapping portions of the spirally wound strips adhere to each other, providing a urinal sheath having an upper portion of thin flexible material designed for application to a penis for covering a substantial portion thereof lengthwise and having a lower thicker portion for connection through a suitable conduit to a urine receptacle, the thinner portion being rolled up until the rolled portion is adjacent the conical portion;

applying the rolled sheath to the penis with the lower thicker portion adjacent the glans of the penis and unrolling said sheath until the sheath extends over and beyond the uppermost edge of the spirally wound pad, and applying squeezing pressure to the outer surface of the sheath to cause it to adhere circumferentially to the spirally wound liner pad, and to press the various elements into closely adhering contact including the contact between the sheath and the overlapped portions of the spirally wound pad to effect a liquid tight seal.

2. The method of claim 1 in which the thicker portion of the sheath has a conical portion, the internal wall of which is placed against the glans of the penis prior to unrolling the sheath.

* * * * *